United States Patent [19]

Miksits et al.

[11] Patent Number: 5,527,519
[45] Date of Patent: Jun. 18, 1996

[54] FINELY DIVIDED, HIGHLY PURE NEUTRAL ZINC OXIDE POWDER, A PROCESS FOR ITS PREPARATION AND ITS USE

[75] Inventors: Michael Miksits, Duisburg; Christoph Tiburtius, Cologne; Jürgen Kischkewitz, Ratingen; Kai Bütje, Duisburg; Albrecht Warth, Mülheim; Franz Herzig, Krefeld; Roland Langner, Bevern, all of Germany

[73] Assignees: Bayer Aktiengesellschaft; Haarmann & Reimer GmbH, both of Germany

[21] Appl. No.: 164,251

[22] Filed: Dec. 7, 1993

[30] Foreign Application Priority Data

Dec. 18, 1992 [DE] Germany ............... 42 42 949.8

[51] Int. Cl.$^6$ ................ C01G 9/02; A61K 7/42
[52] U.S. Cl. ........................ 423/622; 424/59
[58] Field of Search ................. 423/622; 424/59

[56] References Cited

U.S. PATENT DOCUMENTS 2,144,299  1/1939  Sessions et al. .................. 23/55
4,842,832  6/1989  Inoue et al. .................. 423/610

FOREIGN PATENT DOCUMENTS

| 0317272 | 5/1989 | European Pat. Off. | 423/622 |
| 825543 | 12/1951 | Germany | 423/622 |
| 55-42282 | 3/1980 | Japan | 423/622 |
| 57-209824 | 12/1982 | Japan | 423/622 |
| 4280814 | 10/1992 | Japan | 423/622 |

OTHER PUBLICATIONS

Derwent Publications, Abstract No. 92–378833 of JP 4 280 814, Oct. 6, 1992.
Patent Abstracts of Japan, vol. 4, No. 77 of JP 55 042 282, May 4, 1980.
Derwent Publications, Abstract No. 83–131189K of JP 57 209 824, Dec. 23, 1984.

*Primary Examiner*—Shelley A. Dodson
*Attorney, Agent, or Firm*—Connolly & Hutz

[57] ABSTRACT

The invention relates to finely divided, highly pure neutral zinc oxide powder used for UV protection in cosmetic sun screen preparations and daytime skin care preparations as well as in lacquers and plastics, and to a process for its preparation.

15 Claims, 1 Drawing Sheet

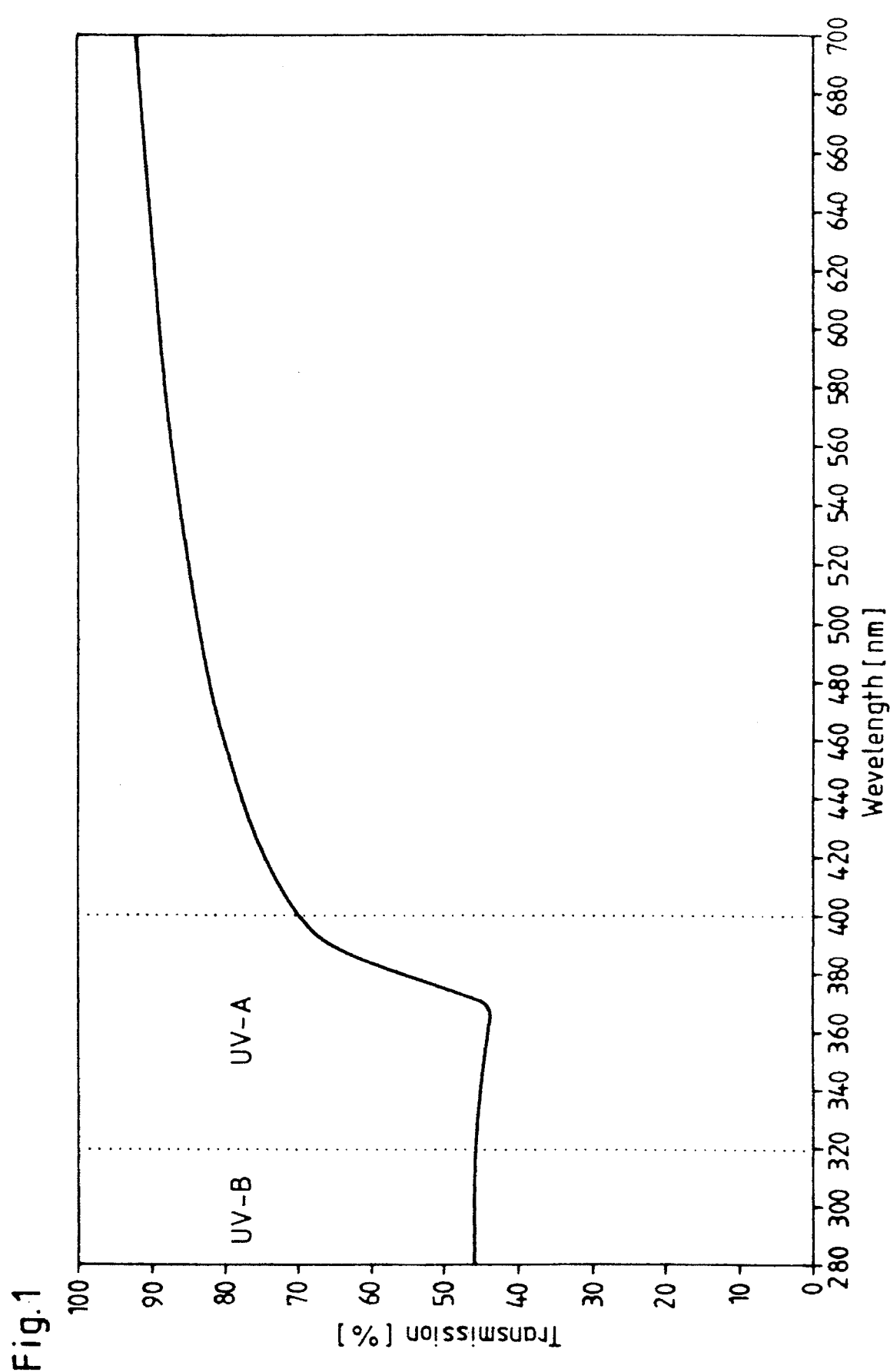

FINELY DIVIDED, HIGHLY PURE NEUTRAL ZINC OXIDE POWDER, A PROCESS FOR ITS PREPARATION AND ITS USE

This invention relates to finely divided, highly pure neutral zinc oxide powder used for UV protection in cosmetic sun screen preparations and daytime skin care preparations as well as in lacquers and plastics, and to a process for its preparation.

It has become increasingly well known for some years that the ultraviolet component of sunlight may cause damage to unprotected skin, ranging from acute sunburn (erythema) and premature aging phenomena to skin cancer. The relatively shortwave component, generally referred to as UV-B, between about 280 and 320 nm, is considered to be primarily responsible for acute damages while it is particularly the longer wave component known as UV-A between about 320 and 400 nm which is considered responsible for premature aging of the skin.

Some screen preparations and products for daytime skin care with UV protection protect the skin against one or both of the ultraviolet radiation components by absorption and/or reflection (scattering). For the UV-B range there exists a broad palette of organic compounds usually referred to as UV filters, which are used on a large scale. The choice of filters for the UV-A range is by comparison very limited. Some of the organic substances used for this range may entail considerable problems of solubility, stability and tolerance by the skin.

As a way out of this situation, finely divided inorganic pigments have for some years been used to a rapidly increasing extent as absorbents and scatterers in the UV-A range. Titanium dioxide in the rutile modification and zinc oxide are particularly considered for this purpose on account of the position of their absorption edges, and zinc oxide is superior to titanium dioxide by virtue of its better properties of dispersibility, which in contrast to $TiO_2$ lead to transparent layers in the visible region of the spectrum.

Zinc oxide powder may be used alone or in combination with UV-B filters, in which case so-called UV broad band protection is obtained. This is known from the literature.

JP 60/231 607, for example, discloses sun screen preparations which contain, as their active constituent, from 1 to 30% by weight of finely divided ZnO having a maximum particle diameter below 0.1 μm and an average diameter from 10 to 60 nm. Preparations containing from 1 to 25% by weight of zinc oxide having an average particle size of from 70 to 300 nm are described in DE 3 642 794. Application JP 62/084 017 discloses cosmetics containing from 0.05 to 30% by weight of transparent zinc oxide having particle sizes < 300 Å.

It is also known to use zinc oxide which has been inorganically after-treated as described in JP 03/183 620 as well as zinc oxide in combination with UV-B filters selected from cinnamic acid esters (DE 2 533 497), dibenzoylmethane derivatives and para-aminobenzoic acid derivatives (JP 61/215 314 and JP 61/257 915) or $TiO_2$ (EP 433 086; sun screening agent containing 2 to 25% by weight each of ZnO and rutile $TiO_2$). ZnO may also be used as a mixture with organic high molecular weight powders or as coating on such powders as described, for example, in JP 03/200 721 and JP 02/049 717.

Finely divided zinc oxide for cosmetic uses must fulfil various requirements. Firstly, it must provide sufficient protection against UV irradiation by UV absorption and must at the same time be as transparent as possible in the visible range in order not to leave a cosmetically unattractive white film on the skin. There is an optimum particle size for optimum protection, as described, for example, in DE 3 642 794. Further, the proportion of heavy metal ions must not exceed a certain level if the product is to satisfy the requirements of the health tests.

Of the three technical processes described in the literature for the preparation of zinc oxide, the so-called French, American and wet chemical process (Ullmanns Enzyklopädie der technischen Chemie, 4th Edition, Volume 24, pages 635 et seq), the latter is particularly suitable for the preparation of finely divided zinc oxide. Although a dry process which is capable of providing finely divided ZnO having a specific surface area of e.g. 25 $m^2/g$ has been proposed in JP 01/286 919, this process presupposes elaborate purification of the starting materials if unacceptably high heavy metal contents are to be avoided in the end product.

The wet chemical process consists in principle of a reaction of a zinc salt solution with an excess of an aqueous alkali metal or ammonium hydroxide or carbonate solution to precipitate a zinc hydroxide or basic zinc carbonate which is converted into zinc oxide by a heat treatment (calcination).

Examples of such processes are described in German Patent Specifications 2 404 049, 825 543, 744 937, 527 167 and 481 284 and in U.S. Pat. No. 2,144,299. These examples, however, also show that for obtaining a finely divided, highly pure zinc oxide having a large specific surface area it is essential to observe quite specific conditions.

Other processes for the preparation of highly pure, finely divided ZnO such as those described in JP 02/129 135 and WO 92/13517, which start from zinc alkoxides or zinc alkylene, use expensive starting materials and are therefore uneconomical. The precipitation and decomposition of zinc oxalate proposed in JP 57/205 319, JP 57/209 824 and JP 03/050 119 also fails to provide any specific advantages over the precipitation of carbonate.

The preparations hitherto obtainable have, however, the disadvantage that they to some extent attack the skin when used and that the zinc oxide contains too high a proportion of metal ion impurities. Moreover, some of the preparations are not sufficiently stable.

It was therefore an object of the present invention to provide a finely divided zinc oxide powder with large specific surface area which contains little or no metal ion impurities, is neutral in reaction, causes no irritation to the skin when used in cosmetic preparations and gives rise to stable products, and to a process for its preparation.

The invention relates to a finely divided, highly pure neutral zinc oxide powder for UV protection, characterised in that it has a specific BET-surface area of from 30 to 100 $m^2/g$ and a pH of from 6.0 to 7.6 according to DIN ISO 787, Part 9, and an exceptionally low heavy metal content amounting to less than 5 ppm of any of the elements Co, Ni, Pb, Cd, Cu, Mn, Fe and Hg.

The specific surface area is determined by the BET-method (DIN 66 131; see also F. M. Nelson, F. T. Eggertsen, Analyt. Chem. 30 (1958), 1387 or S. J. Gregg, K. S. W. Sing, Adsorption, Surface Area and Porosity, London New York 1967, Chapt. 2, 8; adsorption of nitrogen at 77K).

The average primary particle diameter of the zinc oxide powder is normally from 5 to 100 nm.

The zinc oxide powder preferably has an inorganic after-treatment layer consisting of one or more hydroxides, hydrous oxides or oxides of the elements aluminum, silicon, zirconium or titanium in a quantity of from 0.5 to 15% by weight, based on ZnO.

Hydrophobic zinc oxide powder is particularly preferred. Silicone oils are preferably used as hydrophobicising agents.

The invention further relates to stable dispersions of zinc oxide powder in an aqueous or an oily phase selected from mineral, vegetable or animal oils or long chain hydrocarbon compounds or esters, characterised in that they contain from 0.1 to 50% by weight of the zinc oxide powder according to the invention.

The invention also relates to cosmetic preparations such as, for example, suntan creams and lotions and creams and lotions for daytime skin care with UV protection, characterised in that they contain from 0.5 to 20% by weight, preferably from 0.5 to 5% by weight, of the zinc oxide powder according to the invention, either alone or in combination with one or more inorganic and/or organic active substances protecting against UV radiation.

The invention further relates to a process for the preparation of the zinc oxide powder according to the invention by the precipitation of basic zinc carbonate from optionally prepurified zinc sulphate and/or zinc chloride solutions by means of alkali metal carbonate solutions, characterised in that the precipitation is carried out batchwise by introducing the zinc salt solution into the reaction vessel and adding the alkali metal carbonate solution or continuously by simultaneously introducing the solution of zinc salt and of alkali metal carbonate at a pH of from 5.2 to 6.5, preferably from 5.8 to 6.3, and in that the precipitation product is separated from the mother liquor, optionally washed, calcined and ground.

After precipitation, the filtrate is preferably worked up at a pH above 6.5 by the addition of a further quantity of alkali metal carbonate solution and the precipitate obtained from this second precipitation is returned to the process after it has been separated from the mother liquor and redissolved in acid.

The precipitation temperature is preferably from 50° to 90° C., most preferably from 60° to 80° C.

The solutions put into the process preferably contain from 5 to 20% by weight of alkali metal carbonate and 30 to 130 g of zinc/l. The alkali metal carbonate solution used is preferably sodium carbonate solution.

It is particularly advantageous to subject the zinc oxide to an inorganic after-treatment after the calcination.

After calcination or after the inorganic after-treatment, the zinc oxide may also be rendered hydrophobic. The hydrophobicising agents used are preferably silicone oils.

The zinc oxide powder according to the invention is used as UV protective component in cosmetic preparations, in particular in sun screen preparations.

The zinc oxide powder according to the invention is also used as UV protection component in plastics and lacquers.

The finely divided zinc oxide available on the market, which is prepared by the known wet chemical process, normally contains impurities in the form of residues of foreign metal oxides and/or free carbonate. These impurities may cause an alkaline reaction. Such an alkaline reaction has an adverse effect on the properties of the zinc oxide in cosmetic preparations. An alkaline reaction is undesirable in sun-screen and daytime skin care products as it may cause irritation of the skin as well as considerably impairing the stability of the preparation.

Although the alkaline pH of the formulation may be lowered by the addition of components which are acid in reaction, this effect is very frequently accompanied by a marked reduction in the stability of the emulsion. Experiments carried out to produce an organic coating on the surface of ordinary commercial finely divided zinc oxide which is alkaline in reaction, for example by treating the zinc oxide with a hydrophobicising silicone oil, failed to produce the desired stabilization of pH in the neutral region.

The pH may also be important when zinc oxide is used in lacquers and plastics to which the zinc oxide is added as UV protective component if the polymers on which these lacquers and plastics are based are degraded or destroyed by components which are alkaline in reaction.

None of the processes so far known from the literature has been capable of giving rise to a zinc oxide powder capable of fulfilling all the requirements for fineness of subdivision, purity and neutrality of reaction as well as being economical to carry out.

With the continuous processes described in DE 2 404 049 and DE 744 937, in which precipitation is carried out at pH values of from 7 to 10 or 6.5 to 8, it is not possible to obtain an end product which is neutral in reaction.

According to DE 825 543, basic zinc carbonate is precipitated from highly diluted $ZnSO_4$ solutions present in an excess of 2 to 5% by means of sodium carbonate solution at 35° to 45° C. The high dilution renders the process uneconomical and the basic zinc carbonate precipitate is difficult to filter and wash and normally not sufficiently pure.

According to DE 527 167, a slight excess of zinc salt solution at a concentration of at most 1.5N is added to a carbonate solution which is at a concentration of at most 1.5N. Here again, the low concentration results in low volume/time yields and gives rise to problems of effluent. Moreover, the precipitate contains impurities which are alkaline in reaction.

In DE 481 284 and U.S. Pat. No. 2,144,299, a treatment with carbonic acid or with chloride, nitrate or sulphate solution is proposed for purifying the basic zinc carbonate precipitate. Additional foreign ions are thereby carried into the reaction mixture and the process becomes technically very difficult.

According to JP 03/199 121, a finely divided zinc oxide powder is obtained by the addition of a zinc salt solution to an aqueous ammonium carbonate or bicarbonate solution and calcination of the precipitate. Apart from the higher cost of the ammonium carbonates used for precipitation compared with the cost of sodium carbonate, this process has the disadvantage of producing an ammonium salt solution as by-product which is very difficult to dispose of in an environmentally acceptable manner.

According to JP 04/164 813, 04/164 814, 04/164 815 and 04/164 816, finely divided zinc oxide is obtained by the reaction of zinc salt solutions with alkaline solutions at temperatures above 60° C. and pH values above 9, but such zinc oxide powders are always alkaline in reaction.

In the process according to the invention, the precipitation of zinc may be preceded by a purification step already described in U.S. Pat. No. 2,402,371, in which the oxidizable heavy metal ions $Mn^{2+}$ and $Fe^{2+}$ are oxidized by a treatment with chlorine and sodium hydroxide solution and precipitated all together in the form of their hydrous oxides and separated off. Unwanted heavy metal ions ($Co^{2+}$, $Ni^{2+}$, $Pb^{2+}$, $Cu^{2+}$, $Cd^{2+}$ and $Hg^{2+}$) may, also be precipitated by cementation with metallic zinc and removed.

One essential feature of the process according to the invention is that precipitation of the total quantity of zinc takes place in two stages, reaction of the optionally prepurified zinc salt solution with the carbonate solution being carried out in the first stage at a pH of from 5.2 to 6.5, preferably from 5.8 to 6.3.

It was surprisingly found that it is only in this very narrow pH range that the precipitation product obtained is one which after the usual further processing results in a neutral zinc oxide with pH values of from 6.0 to 7.6 according to DIN ISO 787, Part 9. It is essential not to exceed the pH range according to the invention at any stage of the precipitation because zinc oxides with pH values which are too high otherwise result. At lower pH values, on the other hand, only low yields are obtained and basic zinc sulphates and/or chlorides are precipitated at the same time.

The zinc carbonate from the first stage of precipitation is separated from the mother liquor in accordance with the invention, e.g. by filtration, and then worked up to the zinc oxide powder according to the invention by calcination, optionally preceded by washing. The calcination is preferably carried out at temperatures of from 350° to 500° C., most preferably at 400° to 450° C., for obtaining a finely divided zinc oxide powder which is neutral in reaction and has a BET surface area of from 30 to 100 m²/g.

A further quantity of alkali metal carbonate solution may be added in excess to the filtrate from the first precipitation, which still contains zinc in solution, in order that a second precipitation may be carried out at pH values above 6.5. It is immaterial in what sequence the solution and the precipitating agent are added together and exactly at what pH precipitation takes place. The product from the second precipitation is preferably filtered off, dissolved in acid and returned to the process. Alternatively, the product from the second precipitation may be calcined after filtration and washing. The zinc oxide thus obtained, however, does not have the properties according to the invention and therefore cannot be used in accordance with the invention.

Precipitation of zinc carbonate in the first stage of precipitation may be carried out continuously or batchwise. In a continuous process, zinc salt solution and carbonate solution are both introduced into a reaction vessel at the same time, advantageously with pH control. Both this measure and intensive mixing of the components can ensure that the pH range according to the invention is maintained during precipitation.

In a batchwise process, one of the starting solutions may be introduced into the reaction vessel and the other added thereto but the zinc oxide according to the invention is only obtained by the batchwise process if the zinc salt solution is first introduced into the vessel and the carbonate solution is then added until the pH according to the invention is obtained. Here again pH regulation with intensive mixing is advisable. In the reverse case, i.e. if the carbonate solution is first introduced and the zinc salt solution is added thereto, a basic zinc carbonate is obtained which when worked up does not give rise to the zinc oxide according to the invention.

Precipitation of the basic zinc carbonate in the first precipitation stage is preferably carried out at temperatures of from 50° to 90° C., most preferably at 60° to 80° C. Under these conditions, more highly concentrated starting solutions may be used without incurring the risk of unwanted thickening of the contents in the reaction vessel. The precipitation product obtained can easily be filtered and washed.

The solutions used generally contain from 5 to 20% by weight of alkali metal carbonate or 30 to 130 g of zinc/l. Highly concentrated solutions are preferred for economical reasons although less concentrated solutions are preferred for more accurate adjustment of the pH. Sodium carbonate (soda) solutions are preferably used for precipitation, again for economical reasons.

The zinc oxide powder according to the invention may, if desired, be subjected to an organic and/or inorganic aftertreatment before its incorporation in cosmetic preparations or in lacquers or plastics. An inorganic after-treatment may consist, for example, in precipitation of a layer of one or more oxides, hydroxides or hydrous oxides of the elements silicon, aluminium, titanium or zirconium on the zinc oxide. Such an after-treatment layer should not contain less than 0.5% by weight and not more than 15% by weight of such oxides, hydroxides or hydrous oxides.

The zinc oxide powder or the powder which has been inorganically after-treated may also be provided with an organic after-treatment layer, in which case it may be advantageous in particular to carry out a treatment with a silicone oil to render the powder hydrophobic and improve its dispersibility in oleophilic media. The silicon-isation may be carried out by spraying the powder with a suitable silicone oil or by suspending it in the solution of a suitable silicone oil in a low boiling solvent and distilling off the solvent.

The dispersions according to the invention may contain other finely divided pigments, e.g. titanium dioxide, or fillers or organic UV filters in addition to the zinc oxide powder according to the invention.

The cosmetic preparations according to the invention, for example sunscreen creams and lotions or creams and lotions for daytime skin care containing the finely divided, neutral zinc oxide powder at a concentration of from 0.5 to 20% by weight, preferably from 0.5 to 5% by weight, provide the skin with good protection against UV radiation and are distinguished from preparations containing conventional zinc oxide which is alkaline in reaction by their improved stability and tolerance by the skin. In these preparations, the zinc oxide powder may be combined with other UV filters or with inorganic, finely divided pigments such as titanium dioxide.

The invention will now be explained in more detail with the aid of the following Examples.

EXAMPLES

Example 1

Batchwise preparation of the zinc oxide powder according to the invention 5 liters of a zinc sulphate solution (97 g Zn/l) which had been purified by treatment with sodium hydroxide solution and chlorine was diluted with an equal quantity of distilled water and heated to 60° C. and 2.9 liters of a sodium carbonate solution (19% by weight $Na_2CO_3$) were added within 20 minutes with stirring while the temperature was maintained at 60° C. The pH was 5.9 immediately after precipitation and 6.0 after stirring for 30 minutes. The precipitate of basic zinc carbonate was filtered off, washed, dried and calcined for one hour at 430° C. 472 g of a neutral zinc oxide powder having the properties shown in Table 1 were obtained.

Comparison Example 1

Batchwise method

The procedure was the same as in Example 1 but precipitation was carried out at a pH of up to 6.7 immediately after termination of the addition of sodium carbonate and 6.8 after 30 minutes' stirring. 617 g of an alkaline zinc oxide powder having the properties listed in Table 1 were obtained.

EXAMPLE 2

Continuous preparation of the zinc oxide powder according to the invention

The procedure was similar to that of Example 1 but the dilute zinc sulphate solution and the sodium carbonate solution were introduced simultaneously into a reaction vessel at such a speed that the pH was from 6.2 to 6.3 at 60°

C. The properties of the resulting zinc oxide powder are shown in Table 1.

Comparison Example 2

Continuous method

The procedure was the same as in Example 2 except that precipitation was carried out at a pH of from 6.7 to 6.8. The properties of the resulting zinc oxide are shown in Table 1.

TABLE 1

|  | ZnO content % | MgO content % | $SO_4^{2-}$ content % | pH | BET $m^2/g$ |
|---|---|---|---|---|---|
| Example 1 | 94.3 | 0.06 | 2.55 | 7.1 | 66 |
| Comparison Example 1 | 93.0 | 1.11 | 1.30 | 9.7 | 67 |
| Example 2 | 96.7 | 0.17 | 1.20 | 7.1 | 63 |
| Comparison Example 2 | 95.2 | 0.79 | 0.13 | 10.3 | 54 |

EXAMPLE 3

Batchwise industrial experiment

4 $m^3$ of zinc sulphate solution containing 95 g of Zn/l were introduced into an industrial cylindrical tank measuring about 4 m in diameter and about 3 m in height and equipped with a propeller stirrer, and the contents were heated to 60° C. by direct introduction of steam. 8% by weight of aqueous soda solution was then introduced with stirring until, about 20 minutes later, a pH of 6.3 was obtained. The amount of soda solution which had been added up to that point was less than stoichiometric, based on the precipitation of zinc as basic zinc carbonate, so that about 1 g of Zn/l remained unprecipitated in solution.

The product of precipitation was separated on a rotary filter and the filter cake was washed with deionised water and subsequently suspended in water in another stirrer vessel and filtered on a second rotary filter. The precipitation product thus freed from soluble salts such as sodium and magnesium sulphate was predried in conventional manner and calcined at 400° C. in an indirectly heated rotary tubular furnace.

The properties of the end product obtained are shown in Table 2.

An excess of 8% soda solution was added in another stirrer vessel to the filtrate from the first filtration, which still contained dissolved zinc, until a pH of 8 was obtained, leaving a residue of dissolved zinc amounting to 5 mg/l. This suspension was then filtered through a filter press and the filter cake was removed and dissolved in hydrochloric acid and the dilute zinc chloride solution thus obtained was returned to the starting zinc sulphate solution.

TABLE 2

| ZnO | [%] | 96.8 |
|---|---|---|
| BET | [$m^2/g$] | 38 |
| pH |  | 7.2 |
| MgO | [%] | 0.48 |
| $SO_4^{2-}$ | [%] | 1.6 |
| Cl$^-$ | [%] | 0.013 |
| Cu | [ppm] | <1 |
| Pb | [ppm] | <1 |
| Cd | [ppm] | <1 |
| Mn | [ppm] | <1 |
| Fe | [ppm] | <1 |
| Co | [ppm] | <1 |
| Ni | [ppm] | <1 |

TABLE 2-continued

| Hg | [ppm] | <0.05 |
|---|---|---|
| As | [ppm] | <0.5 |
| Se | [ppm] | <1 |

EXAMPLE 4

Incorporation of the zinc oxide powder according to the invention in an emulsion The zinc oxide powder prepared in Example 1 was incorporated in an oil in water emulsion[1] in a quantity by weight of 5%. After several weeks' storage at room temperature, the pH of the emulsion was 7.4. This pH is accepted for cosmetic protective skin care products.

[1]Oil in Water Emulsion:

| Contents/ Trade Name | Supplier* | CFTA** Name | % (W/W) |
|---|---|---|---|
| Part A: |  |  |  |
| Arlacel 165 | (1) | Glyceryl stearate (and) PEG-100 stearate | 4.00 |
| Eumulgin B 2 | (2) | Ceteareth-20 | 1.00 |
| Lanette O | (2) | Cetearyl alcohol | 3.00 |
| Neo Heoliopan, Type AV | (3) | Octyl methoxy cinnamate | 4.00 |
| Neo Heliopan, Type E 1000 | (3) | Isoamyl p-methoxy cinnamate | 4.00 |
| Neo Heliopan, Type MBC | (3) | 4-Methylbenzylidene camphor | 1.00 |
| Paraffin oil 65 cP | (4) | Mineral oil | 2.00 |
| Myritol 318 | (2) | Caprylic/Capric triglyceride | 5.00 |
| Abil 100 | (5) | Dimethicone | 1.00 |
| Zinc oxide |  | Zinc oxide | 5.00 |
| Solbrol P | (6) (7) | Propylparaben | 0.08 |
| Part B | (2) | Water | 64.92 |
| Water, dist. Veegum Ultra | (6) | Glycerol | 1.50 |
| Glycerin | (6) | Sorbitol | 1.50 |
| Sionit K liquid |  | Methylparaben | 0.20 |
| Solbrol M |  |  |  |
|  | (3) |  |  |
| Part C |  | Fragrance | 0.30 |
| Perfume oil |  |  |  |

Method of preparation:

Part A:

All the contents with the exclusion of zinc oxide are weighed into a stirrer vessel and heated to 70°–75° C. with stirring. Zinc oxide is then added and Part A is homogenised for about one minute.

Part B:

The water is heated to about 90° C. in a separate vessel after the addition of Solbrol M. Veegum Ultra is then added and the contents of the vessel are convened into a dispersion by means of Ultra Turax. Glycerol and Sionit K are then stirred in and Part B is introduced into Part A with stirring.

Part C:

When the emulsion has cooled to about 40° C., the perfume oil is added and the emulsion is cooled to room temperature.

* Supplier:

(1) ICI Speciality Chemicals, Goldschmidtstr. 100, D-4300 Essen 1

(2) Henkel KGaA, Dehydag Cospha, Postfach 11 00, D-4000 Düsseldorf 1

(3) Haarmann & Reimer GmbH, Postfach 12 53, D-3450 Holzminden (4) Hansen & Rosenthal, Heilholtkamp 11, D-2000 Hamburg 60

(5) Th. Goldschmidt AG, Goldschmidtstr. 100, D-4300 Essen 1

(6) Bayer AG, D-5090 Leverkusen, Bayerwerk (7) Erbslöh, Kajen 12, D-2000 Hamburg 11

**CTFA:

CTFA International Cosmetic Ingredient Dictionary, Fourth Edition Published by: The Cosmetic, Toiletry and Fragrance Association, 1101 17th Street, N.W. Suite 300, Wash. D.C. 20036

Comparison Example 3

Incorporation of a ZnO powder into an emulsion

The procedure was the same as in Example 4 but using the strongly alkaline zinc oxide from Comparison Example 1 instead of the zinc oxide powder according to the invention from Example 1. After several weeks' storage at room temperature, the pH of the emulsion was 9.0. This pH is too high for cosmetic skin protective products and is not accepted.

Comparison Example 4

Incorporation of a ZnO powder into an emulsion

The procedure was the same as in Example 4 but a zinc oxide obtained by conventional precipitation (addition of zinc sulphate solution to sodium carbonate solution in reaction vessel, filtration, washing and calcining) and having a pH of about 10.5 (according to DIN ISO 787, Part 9) and a specific surface area of about 50 m$^2$/g was used instead of the zinc oxide powder according to the invention from Example 1. After several weeks storage at room temperature, the pH of the emulsion was 9.4. This pH is too high for cosmetic skin protective agents and is not accepted.

EXAMPLE 5

The zinc oxide powder according to the invention from Example 3 was incorporated into isopropyl palmitate by two hours' dispersion on a Skandex Colour Mixer with glass beads at a concentration of 10% by weight with the addition of 0.5% by weight of soya lecithin. Measurement of the UV-Vis transmission spectrum was carded out in a quartz cuvette with 10 μm layer thickness in spherical geometry (RSA-PE-20 balls of Labsphere), using a Perkin Elmer Lambda 2-spectral photometer. Calibration was carried out against isopropyl palmitate. The spectrum is shown in the Figure.

What is claimed is:

1. A process for the preparation of finely divided, neutral zinc oxide powder comprising a zinc oxide powder having a specific BET-surface area of about 30 to about 100 m$^2$/g, a pH of from about 6.0 to about 7.6 and a low heavy metal content amounting to less than 5 ppm of each of the elements Co, Ni, Pb, Cd, Cu, Mn, Fe and Hg by the precipitation of basic zinc carbonate from optionally prepurified zinc sulphate and/or zinc chloride solutions by means of alkali metal carbonate solutions, comprising carrying out the precipitation batchwise by introducing the zinc salt solution into the reaction vessel and adding the alkali metal carbonate solution or continuously by simultaneously introducing zinc salt solution and alkali metal carbonate solution in a pH range of from about 5.2 to about 6.5, and in that the precipitation product is separated from the mother liquor, optionally washed, calcined and ground and wherein the precipitation temperature is from about 60° to about 90° C. and the calcination temperature range is from 350° to 500° C.

2. The process according to claim 1, wherein the powder has an inorganic after-treatment layer consisting of one or more hydroxides, hydrous oxides or oxides of the elements aluminum, silicon, zirconium or titanium in a quantity of from about 0.5 to about 15% by weight, based on ZnO.

3. The process according to claim 1, wherein said powder is hydrophobic.

4. Zinc oxide powder according to claim 3, further comprising a silicone oil as hydrophobicising agent.

5. A process accordingly to claim 1, wherein the pH range is from about 5.8 to about 6.3.

6. A process accordingly to claim 1, wherein after precipitation, the filtrate is worked up by the addition of a further quantity of alkali metal carbonate solution at a pH above 6.5 and the precipitation product from this second precipitation is returned to the process after it has been separated from the mother liqour and redissolved in acid.

7. A process according to claim 5, wherein the precipitation temperature is from about 60° to about 80° C.

8. A process according to claim 1, wherein the solutions put into the process contain from about 5 to about 20% by weight of alkali metal carbonate and from about 30 to about 130 g of zinc/l.

9. A process according to claim 8, wherein the alkali metal carbonate solution used is a soda solution.

10. A process according to claim 1, wherein the zinc oxide is subjected to an inorganic after-treatment after the calcination.

11. A process according to claim 1, wherein after calcination or after the inorganic after-treatment, the zinc oxide is subjected to a hydrophobicising treatment.

12. A process according to claim 11, wherein the hydrophobicising agent used is a silicone oil.

13. A UV protective composition comprising the zinc oxide powder according to claim 1.

14. A plastic comprising the zinc oxide powder according to claim 1.

15. A lacquer comprising the zinc oxide powder according to claim 1.

\* \* \* \* \*